United States Patent
Lu et al.

[11] Patent Number: 5,957,862
[45] Date of Patent: Sep. 28, 1999

[54] ACUPUNCTURE DEVICE SYSTEM AND METHODS THEREOF

[76] Inventors: Cheng-Liang Lu, 12 Nantucket, Irvine, Calif. 92620; Hosheng Tu, 2151 Palermo, Tustin, Calif. 92782

[21] Appl. No.: 08/980,891

[22] Filed: Dec. 1, 1997

[51] Int. Cl.⁶ .................................................. A61H 39/02
[52] U.S. Cl. ........................................ 600/548; 607/115
[58] Field of Search .......................... 600/548; 607/115, 607/116

[56] References Cited

U.S. PATENT DOCUMENTS

| | | | |
|---|---|---|---|
| 3,894,532 | 7/1975 | Morey | 600/548 |
| 3,897,789 | 8/1975 | Blanchard | 600/548 |
| 3,900,020 | 8/1975 | Lock | 600/548 |
| 5,201,751 | 4/1993 | Cohen | 606/189 |
| 5,295,963 | 3/1994 | Deeks | 604/110 |
| 5,385,150 | 1/1995 | Ishikawa | 600/548 |
| 5,546,954 | 8/1996 | Yamada | 600/548 |
| 5,593,429 | 1/1997 | Ruff | 607/116 |
| 5,688,266 | 11/1997 | Edwards et al. | 606/31 |

Primary Examiner—Robert L. Nasser

[57] ABSTRACT

An improved acupuncture device system comprises applying radio frequency energy to an acupuncture point of a patient for a predetermined time and controlled temperature. An acupuncture needle with at least one conducting zone is used to selectively deliver radio frequency energy to the acupuncture site for therapeutic treatment.

9 Claims, 5 Drawing Sheets

ACUPUNCTURE DEVICE SYSTEM AND METHODS THEREOF

FIELD OF THE INVENTION

The present invention generally relates to improved medical devices and methods for acupuncture and, more particularly, to such devices and methods for heating acupuncture needles inserted in a patient and monitoring controlling the needle temperatures.

BACKGROUND OF THE INVENTION

Acupuncture, which involves treatment of a patient by inserting thin needles into his body at certain specific points, is one of the oldest forms of medical practice and has been used in the Orient for thousands of years. The theory generally accepted by the acupuncture practitioners is that the body has energy in the forms of "Chi" and "Blood", which extends through the body organs and manifests itself on the exterior as points on the skin. Each active point on the skin is called an "acupuncture point" and is very small—in the order of one square millimeter or less. Whenever there is imbalance in the energy forms, a person feels ill. By inserting needles at these acupuncture points and applying certain forms of energy, such as mechanical energy through manual maneuvering of the needles or thermal energy, the energy balance can be restored, and so is the patient's general well-being.

Over the centuries the traditional Oriental medicine has identified a large number of acupuncture points on the human body, which differ slightly in their physical properties. There are several variations in the identification and location of these acupuncture points. Many publications have compilations of the acupuncture points in charts and/or in written descriptions.

Successful acupuncture practitioners often have extensive experience and knowledge and have acquired their skills through years of rigorous training and practicing. A skilled acupuncturist may be able to find the acupuncture points by feeling with his fingers.

In recent years, interest in the methods used by the traditional Oriental medicine, especially acupuncture, has been growing rapidly among physicians as well as patients in the West. Some patients believe that the methods employed by the Oriental medicine are simpler and may in some cases lead to better therapeutic results, as compared to traditional Western methods of diagnosis and treatment. Some patients use them as complementary to the Western medical treatment. An increasing number of researchers have also studied the traditional Oriental medicine using modern techniques to gain better understanding. By electronically measuring certain physical properties, one can obtain the same information as might be obtained by a highly skilled acupuncturist using the traditional methods. Hence, electronic measurement of the acupuncture point activity can provide reproducible information with less extensive operator training in acupuncture.

It has been shown, in patent literature and elsewhere, that the traditional Oriental methods can be modified by using modern electronic devices and energy source providers to achieve the results faster without the loss of effectiveness. Combining the Oriental methods with modern sciences can also give more credence to these treatment methods and make them more acceptable to the Western medical community. Various practitioners have tried application of laser beam (light) and electrical stimulation, in addition to the more traditional pressure (massage) and heat, as an energy source to the selected acupuncture points in an effort to improve the ease and effectiveness of the treatment.

The procedure of applying thermal energy to an inserted acupuncture needle, known as moxibustion, has been practiced in the Orient for centuries and has recently been introduced to the Western countries in conjunction with the art and science of acupuncture. In part, this procedure involves heating the inserted needle by lighting a small amount of dried leaves of Artemisia Vulgaris, or wormwood, attached to the handle of the needle, or by holding the lighted end of a cigar-shaped roll of the dried leaves against the needle. This heating procedure is typically continued for 5 to 20 minutes. It is claimed by practitioners of this procedure that the needles heated in this fashion have an enhanced physiological effect. However, this method of heating is non-selective, uncontrolled, and the heat supplied may not reach exactly the desired point for the most effective therapeutic effect.

Acupuncture treatment using these prior art methods of heating inserted acupuncture needles sometimes produce burns caused by hot ashes falling on the patient. Uneven burning and poorly constituted burning materials cause uncontrolled variations of the applied heat, resulting in variations in treatment effectiveness. A temperature controlled energy provider to simulate said prior effective treatment means is in urgent need.

Application of heat, such as using a heating pad or whirlpool of hot or warm water, is widely practiced in the Western world to treat certain muscle- and joint-related bodily pains. However, there has not heretofore been a combination of acupuncture and such Western medical techniques as heating pads or physical therapy to benefit patients having various aches and pains such as those caused by arthritis, rheumatism, osteoarthritis, gout, migraine, gonarthritis, neuralgia, lumbago and similar muscle and joint problems. A temperature controlled energy provider to selectively target the receiving tissue or muscle sites is particularly important.

U.S. Pat. No. 3,938,526, entitled "Electrical Acupuncture Needle Heater", teaches a method of electrically heating an acupuncture needle that has been inserted into a subject. An electrical heating element thermally coupled to an acupuncture needle is used to heat the needle. The residual heat, even after the acupuncture therapy, may continuously burn the surrounding tissue. Said patent does not disclose the means for heating the acupuncture needle by a controllable radio frequency (RF) powered energy source, which is an on-off mode operation in that the heat is cut off immediately when the RF is turned off. Thus, RF heating of an acupuncture needle is less likely to cause unintentional tissue burns.

Of particular interest to the present invention are RF therapeutic protocols which have proven to be highly effective as used by electrophysiologists for tachycardia treatment, by neurosurgeons for the treatment of Parkinson's disease, and for neurosurgeons and anesthetists for other RF procedures such as Gasserian ganglionectomy for trigeminal neuralgia and percutaneous cervical cordotomy for intractable pains. Radio frequency ablation, which exposes a patient to minimal side effects and risks, is generally performed after locating the treatment sites. Radio frequency energy, when coupled with a temperature control mechanism, can supply precise energy to the needle contact site to obtain the desired temperature for the optimal effects.

U.S. Pat. No. 5,546,954, entitled "Method and Apparatus of Applying High-Frequency Wave Current to Reactive Electro-Permeable Point of Patient", teaches applying high-frequency wave current to an acupuncture needle and the second electrode. Said patent discloses the high-frequency wave current as being controlled within 2–10 mHz for a period of 1 to 10 seconds and within 0.5–7 W output. Said patent does not disclose the use of medium-frequency wave current, such as radio frequency current in the range of 100–1,000 kHz, preferably 300 to 600 kHz at an output power up to 50 W. Said patent does not disclose a temperature control mechanism or algorithm to precisely supply the energy as desired.

U.S. Pat. No. 4,408,617, entitled "Apparatus for Detecting the Acupuncture Points on a Patient and for Applying Electrical Stimulating Signals to the Detected Points", teaches a generator for delivering a sawtooth signal to the needle of a probe. However, said patent does not disclose treatment means using RF energy and/or having a temperature control means after finding an acupuncture point.

Imran in U.S. Pat. No. 5,281,218 teaches a needle electrode attached on a catheter for radio frequency ablation. Though a needle-like electrode is beneficial to ablate a tissue point for deep lesion, it is not disclosed that said needle is possible to make a point contact at the desired depth of acupuncture points, neither discloses a temperature control means for radio frequency therapy.

While an acupuncture procedure using an existing needle with high-frequency wave current has had promising results, the whole needle is exposed to the tissue contact area and the heat is dispersed over a wide range of tissue, resulting in inefficient treatment. Therefore there is a need for a new and improved acupuncture device system using the more controllable radio frequency current within the medium-frequency wave current range for generating precise heat to the desired depth of the acupuncture points. When RF energy is applied to a needle inserted in a patient, the RF energy is released to the tissue in direct contact with the needle. If part of the needle surface is insulated or coated with an insulating material, the RF energy can be released to the tissue only through the uninsulated conducting surface of the needle. By designing a needle with the tip as the conducting surface and the rest insulated, the energy releasing surface can be focused at the desired depth of acupuncture points.

SUMMARY OF THE INVENTION

In general, it is an object of the present invention to provide a method and an improved medical device for generating and controlling the heating, and for monitoring the temperature, of acupuncture needles inserted in a patient.

Briefly, heat is generated by applying radio frequency energy to an acupuncture needle in contact with body tissue. A DIP type electrode which contacts the patient is connected to the Indifferent Electrode Connector on the RF generator. When using an alternating current outlet, the generator should be grounded to avoid electrical interference. Heat is controlled by the power of the RF energy delivered and the delivery duration. A temperature sensor is attached to the needle near the tip, where contact with the tissue to be heated is made.

It is one object of the present invention to deliver the RF energy to the needle. It is another object of the present invention to control the energy delivered at a specified temperature. It is another object of the invention to deliver the energy to the tissue surrounding the conducting surfaces of the needle. It is another object of the invention to deliver the energy to the point at the depth of the acupuncture point. It is still another object of the invention not to deliver the energy to the tissue surrounding the insulated surfaces of the needle.

When RF current is passed through a conventional acupuncture needle, a substantial portion of the current does not pass into the desired site of acupuncture point because of loss of current to the surrounding tissue. Therefore, the heating process is very inefficient because the power is wasted. In addition to waste of power, the nearby tissue may receive undesired heating, causing potential damage to the cells. Therefore, it is highly desirable to partially insulate the needle and focus the energy only to the uninsulated conducting surface of the needle.

In one embodiment, the acupuncture needle system further comprises a temperature sensor and a closed-loop temperature control mechanism and/or algorithm. The location of the temperature sensor means is preferably at the proximity of the tip of the needle.

In a particular embodiment, the length of the conducting surfaces of the needle to the distal tip of the needle is 1 cm or shorter. The total length of the needle can be from 2 cm to 10 cm. The needle comprises at least one conducting surface zone. The cross-sectional shape of the needle for this invention can be a round shape, an oval shape, or teeth wheel to increase the tissue contact surface area. The material for the needle of this invention may consist of conductive metals such as platinum, iridium, gold, silver, stainless steel, Nitinol, or an alloy of these metals.

To enhance biocompatibility, the needle may further comprise coating of an anticoagulant such as heparin on the surface of the needle. It is hypothesized that the coated heparin forms a barrier between the tissue and the needle surface to enhance biocompatibility during acupuncture procedures. In another embodiment, the surface of the needle may be treated with low surface energy substrates, such as Teflon® type fluorinated polymers or hydrogel, to reduce the friction during insertion into and removal from the body. In the case of a fluorinated polymer, said polymer can be deposited on the needle surface via plasma coating technology or the like.

A method for operating a needle having RF energy capability within an acupuncture point comprises percutaneously introducing the needle through an acupuncture point, wherein the needle is inserted by pushing the needle gently forward. When the needle reaches the appropriate depth, it is connected to the RF energy generator through an appropriate connecting cable. The patient is connected to the RF generator through a DIP electrode to form a closed-loop current system. Therefore, radio frequency energy is applied and delivered to the target location through the needles of this invention.

The method and apparatus of the present invention have several significant advantages over other known acupuncture needle systems or techniques. In particular, the needle electrode using controllable RF energy as a heat source in this invention may result in a more efficient acupuncture therapeutic effect which is highly desirable in its intended application.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF EXEMPLARY EMBODIMENTS

Figure 1:
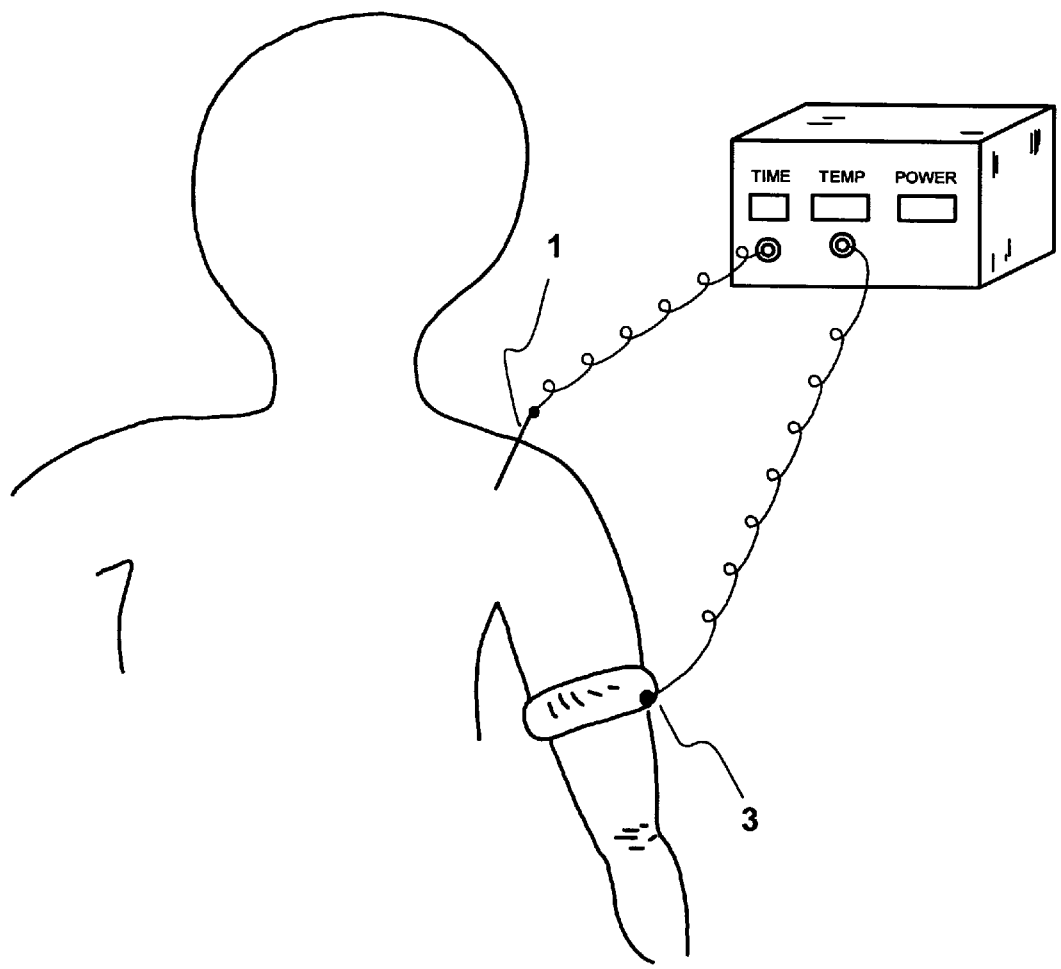
FIG. 1 is a perspective view of an acupuncture system having a needle and an RF generator constructed in accordance with the principles of the present invention.

Referring to FIGS. 1 to 5, there is shown an embodiment of the acupuncture system and a method of applying radio frequency wave to the acupuncture point. As shown in FIG. 1, the acupuncture system comprises an acupuncture needle 1, an RF energy generator 2, and a DIP electrode 3. The needle is inserted to the acupuncture well through the acupuncture point to provide RF energy to the specific site. The "acupuncture point" in this patent is referred to as the skin surface point where the needle is to be inserted into a patient, and the "acupuncture site" is the site where the tip of the needle is to contact the tissue and deliver RF energy. The RF energy generator has the capability to supply RF energy by controlling the time, power and temperature, through a separate closed-loop temperature control means.

Figure 2:
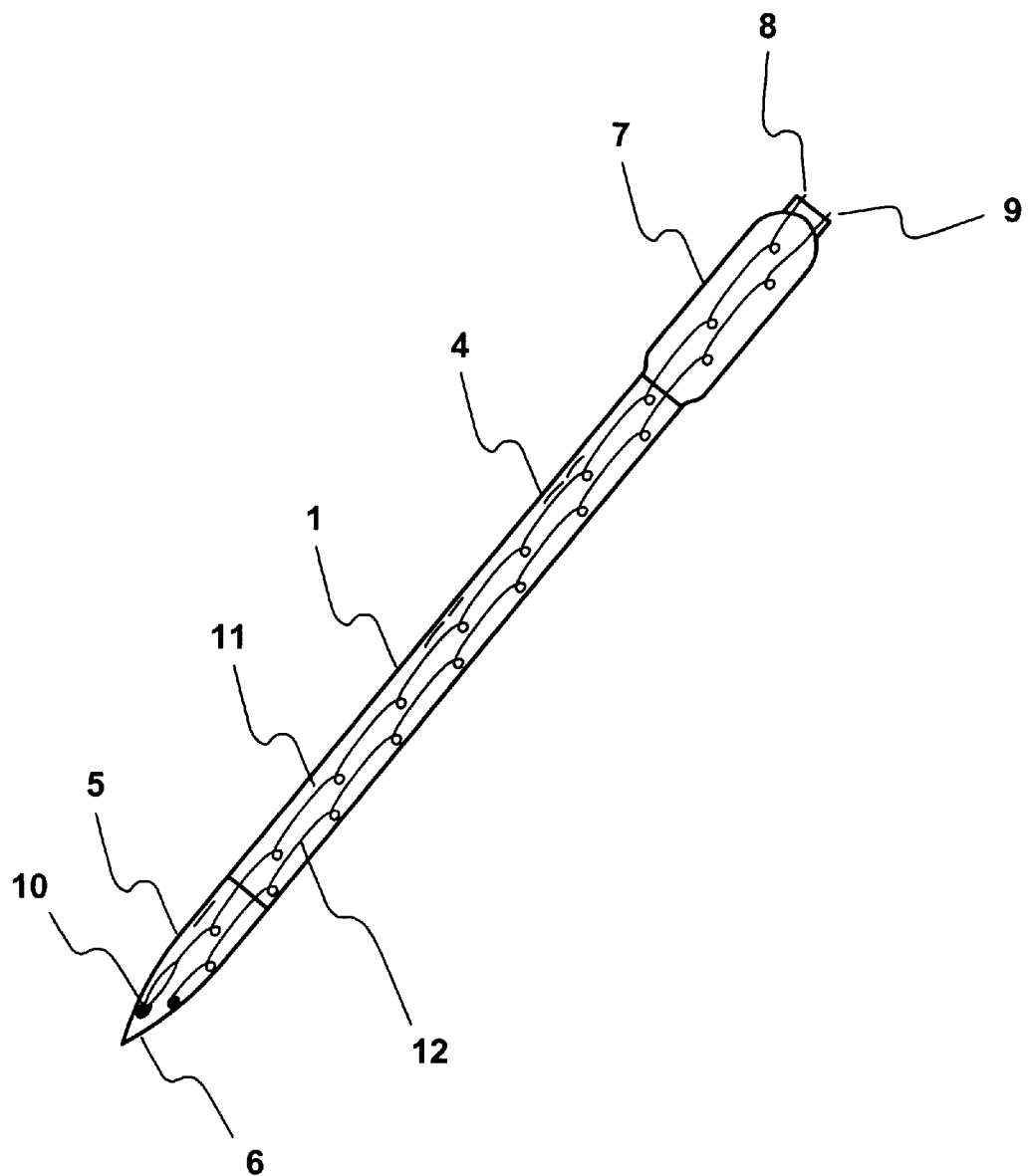
FIG. 2 is a close-up view of the needle in the acupuncture system.

FIG. 2 is a detailed view of the acupuncture needle 1 of the present invention. The needle, which has at least one lumen, comprises the zone of insulated surface 4, the zone of conducting surface 5, the tip 6, and the handle portion 7, wherein said handle portion is not conductive and has a outlet connector 8 for the temperature sensor wire 11 and another outlet connector 9 for RF energy conducting wire 12. In one embodiment, a needle of the present invention comprises at least one zone of conducting surface. A thermocouple type temperature sensor 10 is secured to the tip 6 of the needle 1. The insulated temperature sensor wire 11, which is located within the lumen of the needle, connects the thermocouple 10 to the outlet connector 8. The RF energy conducting wire 12 is secured to the tip 6 of the needle 1 so that the RF energy can be provided to the tip and to the contact tissue via the conducting surface 5 of the needle. The other end of the conducting wire is secured to the connector 9 at the needle handle 7.

Figure 3:
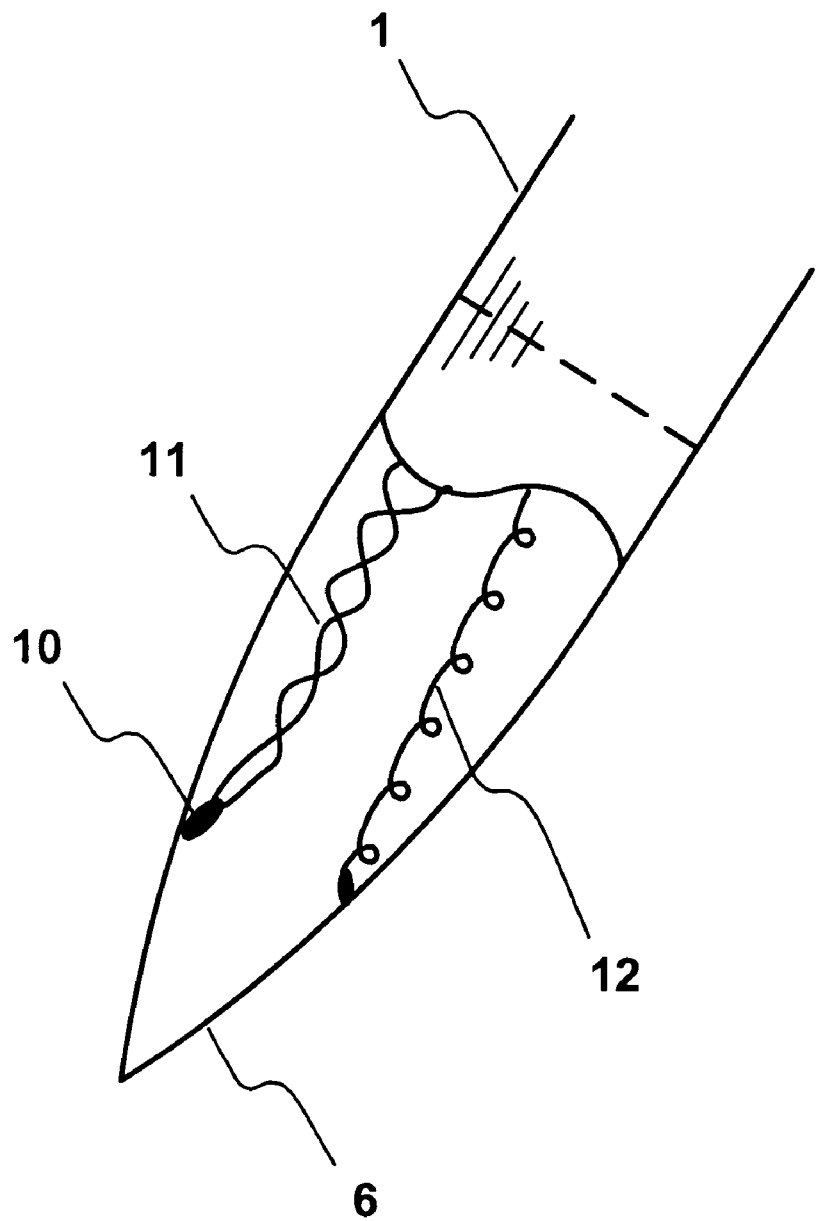
FIG. 3 is a cross-sectional view of the tip section of the needle of FIG. 2.
Figure 4:
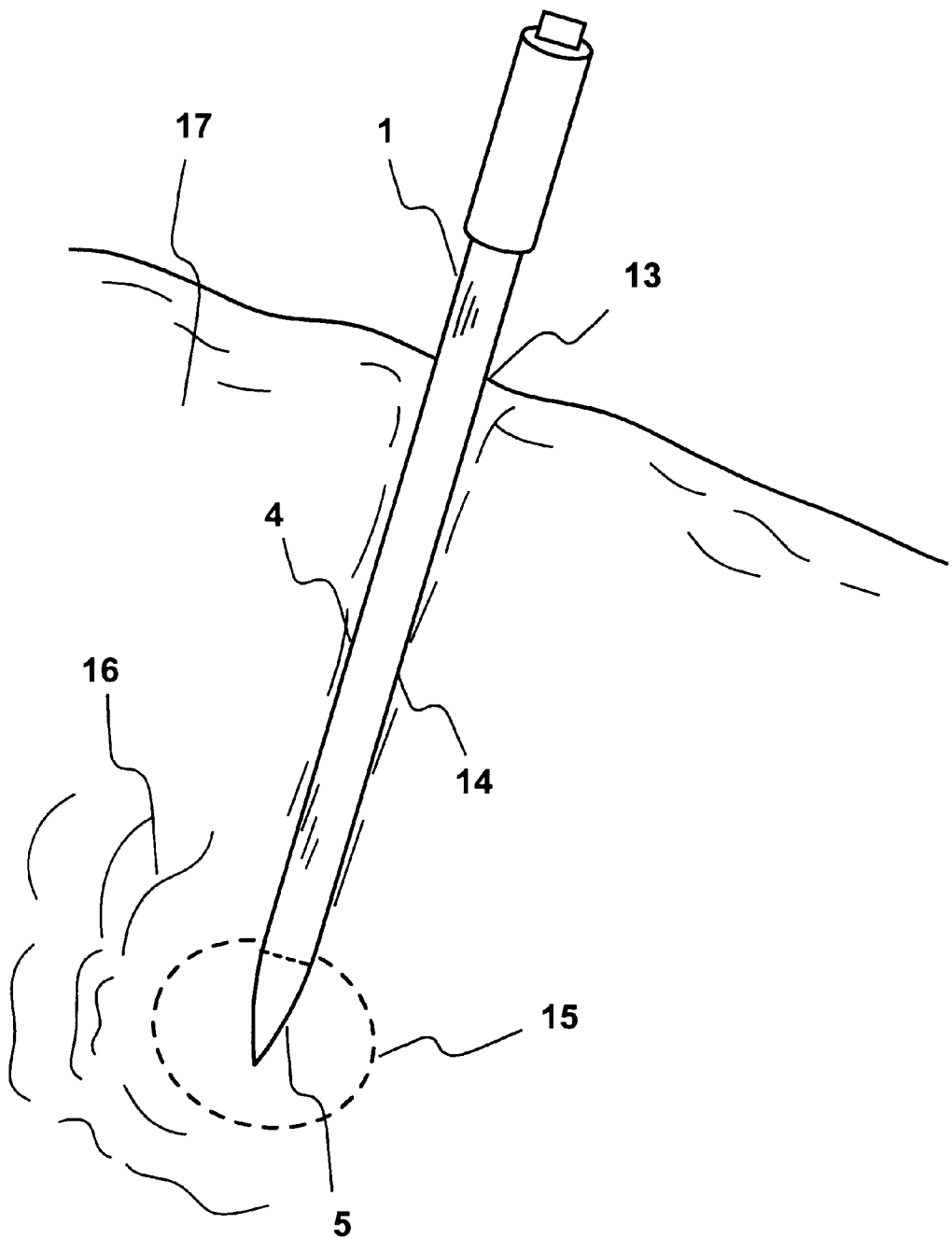
FIG. 4 shows the contact of the needle of the acupuncture system of this invention with the tissue.

FIG. 3 is a detailed view of the tip 6 of the needle 1. FIG. 4 is a simulated view when an acupuncture needle 1 is inserted into the acupuncture point 13 through the acupuncture well 14 to the acupuncture site 15 (the acupuncture site is also generally referred as the "Chi") and contacts the tissue 16. The tissue 17 at the surrounding area does not need any heat. Therefore, a needle with an insulated zone 4 is most appropriate to provide the RF energy heat to the specific site 15 for therapeutic treatment.

Figure 5:
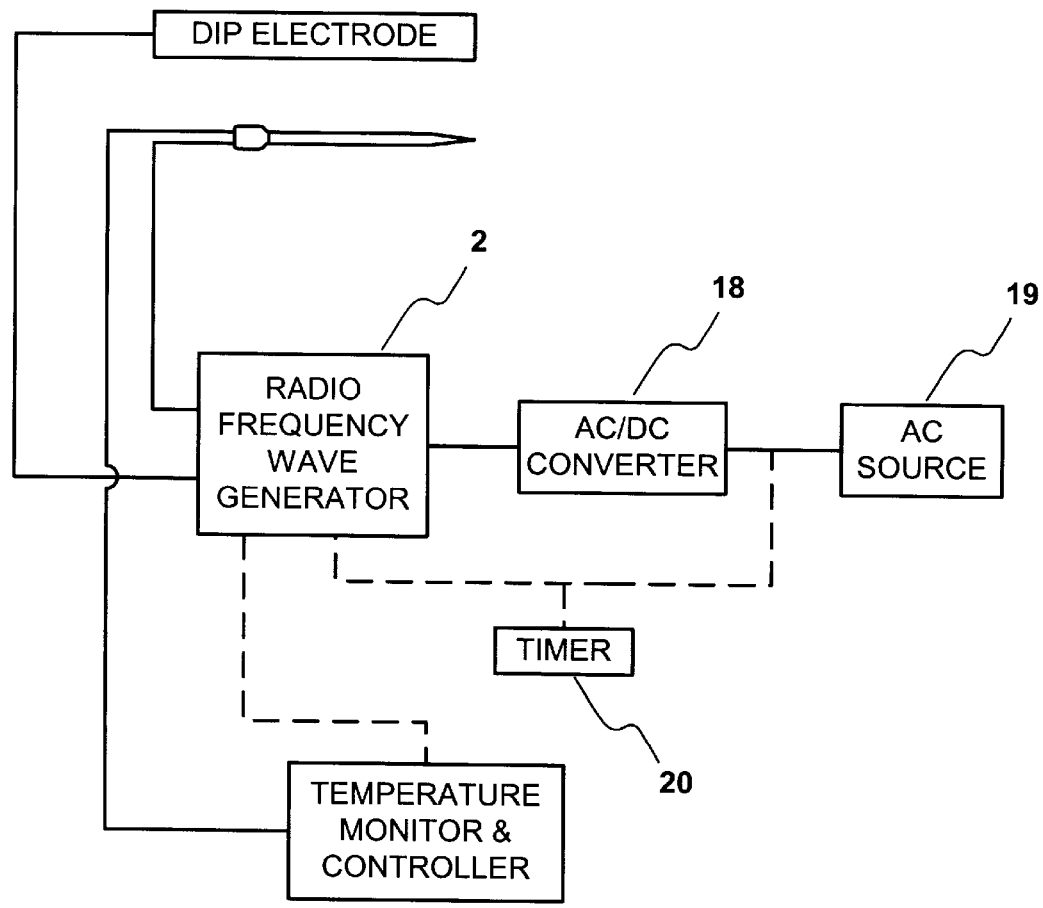
FIG. 5 is a structural view which shows an embodiment of the present invention.

FIG. 5 shows the structural view of the system setup. The radio frequency wave generator 2 receives the DC power source through an AC-DC converter 18. The AC power source 19 is grounded for safety reasons. A timer 20 is installed to control the duration for RF power delivery. A temperature sensor and controller means 21 is included within the generator to supply the heat at a desired temperature to the specific site 15. When the temperature reaches the desired preset point, the power is turned off immediately.

From the foregoing description, it should now be appreciated that an improved acupuncture system comprising a RF generator has been disclosed. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. An apparatus for applying a radiofrequency current to an acupuncture point, comprising:

an acupuncture needle, which is to be inserted into a body of a patient at the acupuncture point, wherein the acupuncture needle a needle distal tip end, a needle body, and a handle at a needle proximal end, and at least one lumen extending between the needle distal tip end and the needle proximal end, the needle distal tip end being conductive over its entire length and the needle body being non-conductive over its entire length;

a connecting cable, said cable being connected to said acupuncture needle;

a DIP electrode, said electrode being adapted to be connected to the body of the patient;

means for generating radiofrequency current; and means for outputting the radiofrequency current from said radiofrequency current generating means to said connecting cable;

a temperature sensor near the needle distal tip end of the needle, wherein the temperature sensor is connected to the radiofrequency current generating means; and a closed-loop temperature control mechanism, wherein temperature readings from the temperature sensor are relayed to the closed loop temperature control mechanism.

2. An apparatus as in claim 1, further comprising surface coating of heparin on said needle.

3. An apparatus as in claim 1, further comprising surface treatment with a low surface energy substrate to reduce friction during insertion and removal of the needle into and from the body of a patient.

4. An apparatus as in claim 3, wherein the low surface energy substrate is selected from the group consisting of fluorinated polymers and hydrogel.

5. An apparatus as in claim 1, wherein the needle is made of a material selected from the group consisting of platinum, iridium, gold, silver, stainless steel, Nitinol, and an alloy of their mixture.

6. An apparatus as in claim 1, wherein a cross-section shape of the needle is one of a round shape, an oval shape, and a wheel-tooth shape.

7. A method of applying radiofrequency current through an apparatus to an acupuncture point of a patient, the apparatus comprising an acupuncture needle which is to be inserted into a body of a patient at the acupuncture point, wherein said acupuncture needle comprises a distal tip end, a body, a handle at a proximal end and at least one lumen extending between the distal tip end and the proximal end the needle distal tip end being conductive over its entire length and the needle body being non-conductive over its entire length; a connecting cable, said cable being connected to said acupuncture needle; a DIP electrode, said electrode being connected to the body of a patient; means for generating radiofrequency current; and means for outputting the radiofrequency current from said radiofrequency current generating means to said connecting cable; means for connecting said DIP electrode to said radiofrequency current generating means; and a temperature sensor near the distal tip end of said needle, wherein the temperature sensor is connected to said radiofrequency current generating means the method comprising the steps of:

(a) inserting an acupuncture needle at an acupuncture point;
(b) connecting the cable from the radiofrequency current generating means to the acupuncture needle;
(c) connecting the DIP electrode from said radiofrequency current generating means to a body of the patient; and
(d) applying a radiofrequency current to the acupuncture needle through the connecting cable.

8. A method as in claim 7, further comprising the step of measuring temperature readings from the temperature sensor.

9. A method as in claim 7, further comprising a closed-loop temperature control mechanism, wherein temperature readings from the temperature sensor is relayed to the closed-loop temperature control mechanism.

\* \* \* \* \*